United States Patent [19]

Megumi et al.

[11] 4,255,557
[45] Mar. 10, 1981

[54] PREPARING POLYCARBONATE OLIGOMERS BY REACTING PHOSGENE WITH AN AQUEOUS SOLUTION CONTAINING A SALT OF A DIHYDRIC PHENOL IN AN ORGANIC SOLVENT WHICH COMPRISES PREVIOUSLY COOLING THE AQUEOUS SOLUTION AND CARRYING OUT THE REACTION AT A LOW TEMPERATURE

[75] Inventors: Takeaki Megumi, Sakai; Hiroyuki Yoshizaki; Sigeo Kondoh, both of Toyonaka, all of Japan

[73] Assignee: Mitsubishi Gas Chemical Company, Inc., Japan

[21] Appl. No.: 81,616

[22] Filed: Oct. 3, 1979

[51] Int. Cl.$^3$ .............................................. C08G 63/62
[52] U.S. Cl. ...................... 528/196; 528/198; 528/200
[58] Field of Search ....................... 528/196, 198, 200

[56] References Cited

U.S. PATENT DOCUMENTS

| | | | |
|---|---|---|---|
| 3,213,059 | 10/1965 | Deanin et al. | 528/200 |
| 3,240,755 | 3/1966 | Cawthon et al. | 528/200 |
| 3,530,094 | 9/1970 | Schnell et al. | 528/198 |
| 4,122,112 | 10/1978 | Koda et al. | 528/196 |

FOREIGN PATENT DOCUMENTS 37-3533 1/1962 Japan .
43-61132 8/1968 Japan .

*Primary Examiner*—Maurice J. Welsh
*Attorney, Agent, or Firm*—Wenderoth, Lind & Ponack

[57] ABSTRACT

A process for preparing polycarbonate oligomers by reacting phosgene with an alkaline aqueous solution containing an alkali metal salt or alkaline earth metal salt of a dihydric phenol in the presence of an inert organic solvent, which comprises previously cooling said alkaline aqueous solution to not higher than 0° C., reacting the cooled aqueous solution with phosgene to perform a phosgenation reaction and also to absorb the heat of the phosgenation reaction by the quantity of heat that said cooled aqueous solution has, thereby to adjust the phosgenation reaction system substantially to not higher than 10° C., and then oligomerizing the phosgenation product at a temperature of 15° C. or higher.

3 Claims, No Drawings

PREPARING POLYCARBONATE OLIGOMERS BY REACTING PHOSGENE WITH AN AQUEOUS SOLUTION CONTAINING A SALT OF A DIHYDRIC PHENOL IN AN ORGANIC SOLVENT WHICH COMPRISES PREVIOUSLY COOLING THE AQUEOUS SOLUTION AND CARRYING OUT THE REACTION AT A LOW TEMPERATURE

This invention relates to a process for preparing a polycarbonate oligomer which is a suitable raw material for a polycarbonate polymer. Specifically, it relates to a process for preparing a polycarbonate oligomer while controlling the temperature, by reacting phosgene with an aqueous alkaline solution containing an alkali metal salt or alkaline earth metal salt of a dihydric phenol in the presence of an inert organic solvent, wherein the phosgenation reaction and the oligomerization reaction are carried out progressively and the heat of reaction generated by the phosgenation reaction is absorbed by the quantity of heat that the reaction system has, namely, latent heat and/or sensible heat, thereby permitting the phosgenation reaction and the oligomerization reaction to be performed in proper temperature ranges. More specifically, the invention provides a process for preparing the oligomers characterized in that the temperature control is effected automatically by a direct heat-exchange method consisting of absorbing the heat of reaction into the reaction system.

The process of the present invention makes it possible to substantially inhibit the hydrolysis of phosgene and chloroformate groups formed by the phosgenation reaction and obtain a polycarbonate oligomer having narrow molecular weight distribution and uniform composition, and further to perform polymerization of the oligomer smoothly and with good reproducibility, thereby affording a high molecular weight polycarbonate having good and stable quality.

Phosgenation method known as one of methods for preparing polycarbonates is generally a process comprising reacting a dihydric phenol with phosgene in the co-presence of an alkali hydroxide, an organic solvent and water to first obtain a comparatively low molecular weight polycarbonate oligomer, and then high-polymerizing the oligomer to obtain a polycarbonate. Various contrivances have hitherto been made for this process for the preparation of a polycarbonate oligomer. For example, there has existed a method comprising introducing phosgene gradually into an ordinary-temperature mixture of an inert organic solvent and an alkaline aqueous solution of a dihydric phenol with stirring. According to this method, the removal (absorption) of the heat of reaction is easy because of the gradual introduction of phosgene, but phosgenation and oligomerization proceed simultaneously, thus broadening the molecular weight distribution of the resulting polycarbonate oligomer, thereby impairing the uniformity of the final polycarbonate. Further, the method cannot avoid the drawback that the ratio of hydrolysis of phosgene and chloroformate groups is high.

Japanese Patent Publication No. 4352/66 proposes a method for preparing oligomers continuously with the use of a packed column type reactor. With this method, the heat of reaction generated by phosgenation is difficult to remove, thus easily causing local overheating. As a result, the ratio of decomposition of phosgene becomes markedly high and the composition and molecular weight distribution of the oligomer become ununiform, thereby making it impossible to perform the polymerization of the oligomer stably and also causing unevenness to the quality of the resulting polycarbonate.

To overcome the difficulty of removing the heat of reaction generated by phosgenation, there has been suggested a method which comprises introducing an inert organic solvent and an alkaline aqueous solution of a dihydric phenol as a mixed-phase stream into a tubular reactor, and passing phosgene therethrough as a parallel flow to absorb the heat of reaction generated as the heat of vaporization of the organic solvent (Japanese Patent Publication No. 21460/71). This method enables the heat of reaction to be removed, but the phosgenation reaction is carried out at an elevated temperature in the vicinity of the boiling point of the organic solvent, thereby entailing the decomposition of phosgene and the oxidative degeneration of the dihydric phenol which would lead to the lowering of the quality of the resulting oligomer.

The present inventors have made eager studies on how to inhibit the hydrolysis of phosgene and chloroformate groups during the preparation of polycarbonate oligomers, and have found that the desired object can be attained by performing a phosgenation reaction such that the contact of an alkaline aqueous solution of a dihydric phenol with phosgene is made at a temperature of not higher than 10° C., preferably not higher than 0° C., and then performing an oligomerization reaction in a temperature range of from 15° C. to the boiling point of the inert organic solvent. It is a novel finding that such progressive execution of the phosgenation reaction and the oligomerization reaction in predetermined temperature ranges permits the hydrolysis of phosgene and chloroformate groups to be substantially inhibited. It is also an unexpected result that said execution affords a polycarbonate oligomer having narrow molecular weight distribution and uniform composition.

The present inventors have made further investigation of how to embody said finding, and have found that since phosgenation by contact of an alkaline aqueous solution of a dihydric phenol with phosgene proceeds very rapidly and the heat of reaction generated thereby is distributed in a very narrow range in terms of both time and space, it is virtually impossible to absorb or remove the heat of reaction by external cooling. In order to remove the heat of reaction promptly by an external cooling method, for example, a very large heat transfer area would be needed. Even if a phosgenation reaction could be performed in a low temperature range by application of strong cooling in said conventional method, energy efficiency in this case would be very low, and an oligomerization reaction would be also dragged into a low temperature range, thus arousing the need to carry out the oligomerization reaction under heat. Thus, this is a scarcely feasible method with great loss of energy.

In view of these facts, the present inventors have conducted investigations on a process for performing phosgenation while maintaining an alkaline aqueous solution of a dihydric phenol and phosgene in contact with each other at a temperature of not higher than 10° C., preferably not higher than 0° C. As a result, they have found that the optimal method is a direct heat exchange method comprising previously cooling said alkaline aqueous solution to not higher than 0° C., and reacting the cooled aqueous solution with phosgene so that the heat of reaction generated violently by phosgenation is absorbed into the reaction system by utilizing the quantity of heat that the cooled aqueous solution has. Here, the quantity of heat that the cooled aqueous solution has refers to the quantity of heat accumulated as sensible heat and/or latent heat. The present inventors have also found that in order to carry out the direct heat exchange method efficiently and suitably, it is desirable to make said alkaline aqueous solution into a partially frozen cold aqueous solution or a cold aqueous solution containing ice and to control the reaction temperature by utilizing the quantity of heat that the cold aqueous solution has, namely, the latent heat of ice and the sensible heat of the reaction system.

The present invention is a process for preparing a polycarbonate oligomer by reacting phosgene with an alkaline aqueous solution of an alkali metal salt or alkaline earth metal salt of a dihydric phenol in the presence of an inert organic solvent, which comprises previously cooling said alkaline aqueous solution to not higher than 0° C., reacting the cooled aqueous solution with phosgene to perform a phosgenation reaction and absorb the heat of reaction of phosgenation by the quantity of heat that said cooled aqueous solution has, thereby to adjust the phosgenation reaction system substantially to not higher than 10° C., and then oligomerizing the resulting phosgenation product at a temperature of not lower than 15° C. More preferably, the invention is a process for preparing a polycarbonate oligomer which involves the use, as the aqueous solution previously cooled to not higher than 0° C., of a cold aqueous solution made by partially freezing the alkaline aqueous solution or rendering ice co-present in the alkaline aqueous solution.

With the process of the present invention using such a cold aqueous solution to perform a phosgenation reaction, the heat of reaction generated by the phosgenation reaction is absorbed into the reaction system by direct exchange of heat, thus promptly preventing the temperature from rising. Therefore, the reaction system is easy to adjust to not higher than 10° C. After a substantial phosgenation reaction has been completed at 10° C. or lower, the reaction mixture automatically reaches 15° C. or higher, or may be easily led to 15° C. or higher, because of the heat of reaction absorbed into it. As described earlier, the temperature suitable for an oligomerization reaction is 15° C. or higher. The cold aqueous solution made by partially freezing the alkaline aqueous solution or by making ice co-present in the alkaline aqueous solution is preferred in practical use in that it can be maintained at a low temperature of from minus 1° C. to minus 9° C. which is the temperature of ice co-present, and in that it has great latent heat which is the heat of fusion of ice.

According to the process of the present invention, the heat of reaction of the phosgenation reaction can be absorbed promptly though the phosgenation reaction is such a rapid reaction as to be completed in seconds, and the phosgenation reaction can be maintained in a temperature range of not higher than 10° C., preferably not higher than 0° C. Therefore, the hydrolysis of phosgene and chloroformate groups can be inhibited substantially, and an oligomerization reaction performed in a suitable temperature range of 15° C. or higher makes it possible to form an oligomer having narrow molecular weight distribution and uniform composition. Also, very low temperatures can be maintained before and after the phosgenation reaction, thus making the starting phenol free from oxidative degeneration. This fact leads to the high quality of the final polycarbonate.

The aforesaid cold aqueous solution made by partially freezing the alkaline aqueous solution or by making ice co-present in the alkaline aqueous solution should desirably have an ice content, expressed in the amount of the frozen portion or ice, within the range of 70% by weight or less based on the total amount of the dihydric phenol, alkali hydroxide and water contained in the cold aqueous solution, but the ice content may be selected suitably in consideration of various factors such as the presence or absence of external cooling for the reactor, the form of phosgene supplied, the type of the solvent, and the concentration of the dihydric phenol in the alkaline aqueous solution. If the concentration of the dihydric phenol is within an usually employed range of from 12 to 16% by weight, it is suitable that the ice content be 10 to 30% by weight. A method of partially freezing the alkaline aqueous solution is not critical, and an example may comprise contacting the alkaline aqueous solution with a scraper-equipped drum type ice making device to freeze part of the aqueous solution, or comprise directly adding a refrigerant to the alkaline aqueous solution to crystallize ice upon its evaporation.

In the present invention, the dihydric phenol includes bis(4-hydroxyphenyl)alkanes known as starting materials for polycarbonates, typified by 2,2-bis(4-hydroxyphenyl)propane and 2,2-bis(4-hydroxy-3,5-dibromophenyl)propane. Alkaline compounds used to form salts of dihydric phenols include alkali metal hydroxides represented by sodium hydroxide and potassium hydroxide, and alkaline earth metal hydroxides exemplified by calcium hydroxide. Said alkaline compound is used in an amount of 1 to 3 moles, preferably 1.3 to 2 moles, per mole of the dihydric phenol.

Examples of the inert organic solvent are known solvents for producing polycarbonates, and specific examples include chlorinated hydrocarbons typified by methylene chloride and 1,2-dichloroethane, and aromatic compounds such as toluene, xylene, and chlorobenzene.

Phosgene may be introduced in a gaseous form or liquid form, but it is preferred to introduce phosgene dissolved in said inert solvent and cooled to not higher than 10° C.

The process of the present invention is advantageous in that it may be performed batchwise or continuously, and that the size of the reactor can be made very small. It is preferred, however, to carry out the process in a continuous manner, in view of the facts that as aforementioned, the removal of heat of the phosgenation reaction is fast and thus is no need for gradual addition of phosgene, that the reaction conditions for phosgenation can be easily led to those for oligomerization, and that even when the reaction system is made into a plug flow by use of a tubular reactor, no trouble occurs.

Polycarbonate oligomers obtained by the process of the present invention are further subjected to a polymerization reaction to be led to polycarbonates having high molecular weights. A polymerization degree regulator for use in the polymerization reaction may have previously been added to the alkaline aqueous solution of the dihydric phenol, or may have previously been dissolved in the organic solvent, or may be added at the time of polymerization of the oligomer.

The process of the present invention will be described below by reference to Examples and Comparative Examples. In these examples, "APHA" is an abbreviation of "American Public Health Association," customarily used to indicate a value showing the degree of coloration of a liquid organic chemical product. 1.246 g of potassium chloroplatinate ($K_2PtCl_6$) and 1.0 g of cobaltous chloride ($CoCl_2 \cdot 6H_2O$) are dissolved in 100 ml of aqueous hydrogen chloride, and the solution is diluted to a total amount of 1 liter. The resulting solution is used as a standard solution. The degree of coloration of this standard solution is represented by a color number of 500, which is expressed as "APHA 500." A standard solution having a color number of 10, for instance, is obtained by diluting said standard solution to 50 times the original volume. Many standard solutions having different color numbers are thus prepared. Two test tubes each of a predetermined size are used for tests. One of the test tubes is charged with a test solution, while the other test tube is charged with a standard solution. Then, both solutions are compared visually, and in view of the results of the comparison, a standard solution having the same degree of coloration as said test solution is determined. The color number of the standard solution corresponds to the value of "APHA" of the test solution.

The test solution in the examples is prepared by dissolving 4 g of the resulting polycarbonate oligomer or high molecular weight polycarbonate in 25 ml of methylene chloride. This test solution is used for measurement of APHA value as described above. The molecular weight distribution is determined from analyses of charts obtained by using a gel permeation chromatograph, ALC/GPC 244, a product of Waters Associate Inc.

Example 1

A beaker having an internal volume of 2 liters was equipped with a stirrer making a reciprocating motion, a thermocouple for temperature measurement, and a phosgene introducing tube having an opening at the height of 5 cm from the bottom of the beaker. 35 Grams of sodium hydroxide and 350 ml of distilled water were placed in the beaker, and agitated. After the sodium hydroxide was dissolved, 91.2 g of bisphenol A was added. The outside wall of the beaker was cooled with ice water to lower the temperature of the solution to 5° C., and then 150 g of crushed ice was added. The alkaline solution of bisphenol A was stirred for 1 minute, and then, a solution of 44 g of phosgene in 250 ml of methylene chloride, which solution had been cooled to 0° C., was added over the course of about 5 seconds through the phosgene introducing tube. The temperature of the mixture, immediately before the phosgene introduction, was −7° C., but rose to 19° C. at the time when the phosgene introduction was completed. This fact showed the phosgenation reaction to be completed within several seconds. Thereafter, agitation was continued for 10 minutes to perform oligomerization reaction. The temperature of the reaction mixture was 25° C.

From the amount of $Na_2CO_3$ in the aqueous layer resulting after the oligomerization reaction and the amount of phosgene introduced, there was determined the total ratio of decomposition of phosgene and chloroformate groups, which once formed, during the synthesis of a polycarbonate oligomer. That total ratio of decomposition was found to be 0.5%.

The organic layer resulting after the oligomerization reaction was collected in a small amount, neutralized and washed with water, followed by distilling off methylene chloride, to obtain a polycarbonate oligomer. The oligomer had an APHA of 10, and its molecular weight distribution pattern showed very sharp peaks.

To a mixture of the organic layer and the aqueous layer that resulted after the oligomerization reaction were added 50 ml of an aqueous solution of sodium hydroxide having a concentration of 20% by weight, and 180 ml of a methylene chloride solution of para-tert-butylphenol having a concentration of 1.0% by weight, and the mixture was subjected to polymerization with stirring. The ratio of decomposition of chloroformate groups during the polymerization was 0.2% based on the amount of phosgene charged. The resulting high molecular weight polycarbonate had an APHA of 10 and its molecular weight distribution was found to be narrow.

Comparative Example 1

Exactly the same apparatus as in Example 1 was assembled, and 35 g of sodium hydroxide and 500 ml of distilled water were placed in the beaker of the apparatus, followed by stirring. After the sodium hydroxide was dissolved, 91.2 g of bisphenol A and 150 ml of methylene chloride were added. The outside wall of the beaker was cooled with cold water so that the temperature of the mixture in the beaker could be maintained at 5° C. 44 Grams of phosgene was dissolved in 100 ml of methylene chloride, and the solution, after cooled to 0° C., was fed gradually over the course of about 15 minutes through the phosgene introducing tube. The reaction mixture during the phosgene feeding was maintained at 5° C., and oligomerization also proceeded simultaneously.

In the same manner as in Example 1, the total ratio of decomposition of phosgene and chloroformate groups during synthesis of a polycarbonate oligomer was determined, and it was found to be 10.7%. This high total ratio of decomposition of phosgene and chloroformate groups was understood to be due to the fact that the temperature range suited to phosgenation was unsuited for oligomerization.

Comparative Example 2

A jacketed tubular reactor having an inside diameter of 10 cm and a length of 150 cm was filled with Rasching rings. The reactor was supplied, from its top, with a mixture of 30.4 kg/hour of bisphenol A, 209.6 kg/hour of an aqueous solution of sodium hydroxide having a concentration of 7% by weight, and 40 g/hour of hydrosulfite, and a mixture of 14.6 kg/hour of phosgene and 133 kg/hour of methylene chloride, both mixtures being at 20° C. The reaction mixture resulting after the oligomerization reaction was taken out from the bottom of the reactor. The temperature of the reaction mixture at the outlet was 27° C.

The total ratio of decomposition of phosgene and chloroformate groups once formed was determined in the same way was in Example 1. It was 13.0%.

Comparative Example 3

Exactly the same apparatus as in Example 1 was assembled, and its beaker was charged with 35 g of sodium hydroxide and 500 ml of distilled water, followed by stirring the mixture. After the sodium hydroxide dissolved, 91.2 g of bisphenol A was added, and the outside wall of the beaker was cooled with water to set the temperature of the mixture inside the beaker at 20° C. A solution, cooled to 0° C., of 44 g of phosgene in 250 ml of methylene chloride was added over the course of about 5 seconds through the phosgene introducing tube. Simultaneously with the initiation of phosgene introduction there was observed violent boiling and evaporation of methylene chloride. After completion of phosgene introduction, the reaction mixture was at 34° C. Then, stirring was continued for 10 minutes to carry out oligomerization reaction. The temperature of the reaction mixture was 28° C.

The total ratio of decomposition of phosgene and once formed chloroformate groups was determined in the same way as in Example 1, and it was found to be 16.2%. The resulting polycarbonate oligomer had an APHA, as measured in the same way as in Example 1, of 15 and its molecular weight distribution was much broader than that of Example 1.

A mixed liquid of the organic layer and aqueous layer resulting after the termination of the oligomerization reaction was polymerized in the same way as in Example 1. The ratio of decomposition of chloroformate groups during the polymerization was 1.5% based on the amount of charged phosgene. The resulting high molecular weight polycarbonate had an APHA of 25, and its molecular weight distribution was considerably broad. From this fact it was seen that the oligomer remained in a large amount.

With the above described method utilizing evaporation of methylene chloride to remove the heat of phosgenation reaction, it was seen that since the phosgenation reaction was performed at an elevated temperature in the vicinity of the boiling point of methylene chloride, hydrolysis of phosgene accompanied.

Example 2

A drum type, scraper-equipped, ice making device having a freezing drum having a diameter of 80 cm and a freezing area of 1.61 m² (V-155, a product of Atlas-Mitsubishi Steel Mfg., Co., Ltd., an ice making capacity 4.2 tons/day), a slurrying pump, a line mixer having an internal volume of 1 liter, and a stirrer-equipped reactor having an internal volume of 150 liters were assembled in this sequence to make a polycarbonate oligomer synthesizing apparatus. A mixed liquid consisting of 1.73 kg/minute of bisphenol A, 10.4 kg/minute of an aqueous solution of sodium hydroxide having a concentration of 5.5% by weight, and 3.6 g/minute of hydrosulfite was fed to the liquid feeding portion of the ice making device. Separately, a mixed liquid consisting of 0.76 kg/minute of phosgene and 5.0 liters/minute of methylene chloride was supplied at 0° C. to one of the inlets of the line mixer. A slurried cold aqueous solution consisting of 2.83 kg/minute of frozen matter at −4° C. and 9.3 kg/minute of an unfrozen liquid at 12° C. was obtained from the outlet of the ice making device. Said slurried solution was guided at −3° C. to the other inlet of the line mixer via the slurrying pump, for contact with the phosgene-methylene chloride solution to perform a phosgenation reaction. The reaction mixture directed to the reactor was discharged from the outlet of the reactor after completion of an oligomerization reaction. The temperature of the discharged mixture was 29° C.

The total ratio of decomposition of phosgene and chloroformate groups, which once formed, during synthesis of a polycarbonate oligomer was 0.3%, and the APHA of the resulting polycarbonate oligomer was 10.

What is claimed is

1. A process for preparing polycarbonate oligomers by reacting phosgene with an alkaline aqueous solution containing an alkali metal salt or alkaline earth metal salt of a dihydric phenol in the presence of an inert organic solvent, which comprises previously cooling said alkaline aqueous solution to not higher than 0° C., reacting the cooled aqueous solution with phosgene to perform a phosgenation reaction and also to absorb the heat of the phosgenation reaction by the quantity of heat that said cooled aqueous solution has, thereby to adjust the phosgenation reaction system substantially to not higher than 10° C., and then oligomerizing the phosgenation product at a temperature of 15° C. or higher.

2. A process as described in claim 1, wherein said alkaline aqueous solution previously cooled to not higher than 0° C. is a cold aqueous solution made by partially freezing said alkaline aqueous solution or a cold aqueous solution made by rendering ice co-present in said alkaline aqueous solution.

3. A process as described in claim 1, wherein said dihydric phenol is at least one member selected from bis(4-hydroxyphenyl)alkanes.

* * * * *

UNITED STATES PATENT AND TRADEMARK OFFICE
CERTIFICATE OF CORRECTION

PATENT NO. : 4,255,557
DATED : March 10, 1981
INVENTOR(S) : Takeaki Megumi, Hiroyuki Yoshizaki and Sigeo Kondoh It is certified that error appears in the above-identified patent and that said Letters Patent are hereby corrected as shown below:

On the title page, add Item [30] to read:

-- Foreign Application Priority Data

October 9, 1978 [JP] Japan .......... 53-124,271 --.

Signed and Sealed this

Twenty-third Day of March 1982

[SEAL]

Attest:

GERALD J. MOSSINGHOFF

Attesting Officer

Commissioner of Patents and Trademarks